United States Patent [19]

Mitra

[11] 4,404,132
[45] Sep. 13, 1983

[54] BLOOD COAGULATION PROMOTING PRODUCT

[75] Inventor: Gautam Mitra, Kensington, Calif.

[73] Assignee: Cutter Laboratories, Inc., Berkeley, Calif.

[21] Appl. No.: 345,988

[22] Filed: Feb. 5, 1982

Related U.S. Application Data

[63] Continuation-in-part of Ser. No. 153,396, May 27, 1980, abandoned.

[51] Int. Cl.$^3$ .................. C07G 7/00; A61K 35/14; A61K 35/16; A61K 37/02
[52] U.S. Cl. .................. 260/112 B; 424/101
[58] Field of Search .................. 260/112 B; 424/101

[56] References Cited

U.S. PATENT DOCUMENTS

| | | | |
|---|---|---|---|
| 3,560,475 | 2/1971 | Fekete et al. | 260/112 B |
| 3,682,881 | 8/1972 | Fekete et al. | 260/112 B |
| 3,717,708 | 2/1973 | Wada et al. | 260/112 B X |
| 4,081,431 | 3/1978 | Stephan et al. | 260/112 B |
| 4,160,025 | 7/1979 | Eibl et al. | 424/101 |
| 4,170,590 | 10/1979 | Stephan et al. | 260/112 B |
| 4,272,523 | 6/1981 | Kotitschke et al. | 260/112 B |
| 4,364,861 | 12/1982 | Mitra et al. | 260/112 B |

OTHER PUBLICATIONS

New England J. of Med., vol. 273, No. 13, 1965, Tullis et al., pp. 667–674.
British J. of Haematology, vol. 22, 1972, pp. 469–490, Dike et al.
Vox Sang. 24, pp. 441–456, (1973), Middleton et al.
Vox Sang. 33, pp. 37–50, (1977), Suomela et al.

Primary Examiner—Howard E. Schain
Attorney, Agent, or Firm—Theodore J. Leitereg; David J. Aston

[57] ABSTRACT

This disclosure pertains to a concentrate for controlling bleeding in hemophilia, free of thrombin, heparin, thromboplastin activity, anticomplement activity, depressor activity, and activated Factor X, and containing coagulation Factors II, VII, IX, and X in non-activated form and containing no greater amounts of calcium-activated factors and Factor VIII Inhibitor Bypassing Activity substance than that found in concentrates of Factor II, VII, IX, and XI that have not been treated, respectively, with calcium or a material which would produce a Factor VIII Inhibitor Bypassing Activity substance in such concentrates and having a specific activity of at least about 1.5 Factor IX units per milligram of total protein and a Factor IX:Factor VII ratio of at least about 6:1, a Factor IX:Factor II ratio of about 1:1 to 2:1, and a Factor IX:NAPTT ratio of at least about 5:1 on a Units per milliliter basis, a Factor II Specific Activity of about 1.0–4.0 Units per milligram of total protein, and a Factor IX:ceruloplasmin ratio of at least about 25:1. In the method of the invention a blood fraction containing coagulation Factors II, VII, IX, and X is applied to an anion exchanger to adsorb the coagulation Factors, which are selectively eluted therefrom using an aqueous sodium chloride-citrate solution of increasing ionic strength. The eluate is treated to reduce its concentration of non-volatile salt and concentrated to yield the above product.

4 Claims, No Drawings

BLOOD COAGULATION PROMOTING PRODUCT

CROSS-REFERENCE TO RELATED APPLICATIONS

This is a continuation-in-part of application Ser. No. 153,396 filed May 27, 1980, now abandoned.

BACKGROUND OF THE INVENTION

1. Field of the Invention

This invention relates to and has among its objects the provision of novel blood coagulation components and novel methods of making them. Further objects of the invention will be evident from the following description.

2. Description of the Prior Art

There are estimated to be 100,000 cases of congenital hemophilia in the United States. Of these, approximately 20,000 are cases of hemophilia B, the blood of such patients being either totally devoid of plasma thromboplastin component or seriously deficient in plasma thrombopolastin component. The disease therefore exists in varying degrees of severity, requiring therapy anywhere from every week up to once or twice a year. The completely deficient cases require replacement therapy once every week; the partially deficient cases require therapy only when bleeding episodes occur, which may be as seldom as once a year. The bleeding episodes in congenital, partially-deficient cases are generally caused by a temporarily acquired susceptibility rather than by injury alone. Intravenous injection of a sufficiently large amount of fresh plasma, or an equivalent amount of fresh blood, temporarily corrects the defect of a deficient subject. The beneficial effect often lasts for two or three weeks, although the coagulation defect as measured by in-vitro tests on the patient's blood appears improved for only two or three days. Such therapy with fresh plasma or fresh blood is effective but it has several serious drawbacks: (1) it requires ready availability of a large amount of fresh plasma; (2) requires hospitalization for the administration of the plasma; (3) a great many of the patients become sensitized to repeated blood or plasma infusions and ultimately encounter fatal transfusion reactions; (4) at best plasma can only partially alleviate the deficiency; and (5) prolonged treatment or surgery is not possible because the large amounts of blood or plasma which are required will cause acute and fatal edema.

Several investigators noted that the mixing of blood of certain hemophilic patients would result in the mutual correction of the clotting defect of each blood. Interpretation of these findings was eventually made by Aggeler and co-workers [*Proc. Soc. Exptl. Biol. Med.* 79:692–696 (1952)] and S. G. White et al. [*Blood* 8:101–124 (1953)]. These workers, studying a male patient with a severe hemorrahagic diathesis associated with a prolonged clotting time which was clinically indistinguishable from classic hemophilia, postulated the existence of a new clotting factor. Aggelar et al., recognizing that the new factor was a precursor of thromboplastin, named it Plasma Thromboplastin Component (PTC). The work was confirmed by Biggs et al. [*Brit. Med. J.* 2:1378–1382 (1952)] in England, who gave it the name Christmas Factor, and by Soulier and Larrieu [*New Eng. J. Med.* 249:547–553 (1953)] in France, who called it Antihemophilic Factor B. This factor is now officially designated Factor IX.

In collaboration with Aggeler et al., the first fractionated PTC preparation was prepared [*Revue d'Hematologie* 9:447–453 (1954)]. The PTC was absorbed on barium sulfate from a solution of Cohn Fraction IV and eluted with 0.34 M sodium citrate. The yields are very small, and the post-infusion in-vivo activity was only about one-fourth that predicted from in-virto assays by a prothrombin consumption test.

Later, in collaboration with Aggeler et al., a process was developed by which PTC was adsorbed onto barium sulfate from EDTA anticoagulated plasma, eluted with a sodium chloride-sodium citrate buffer, and further purified by cold ethanol fractionation. This preparation was used clinically with excellent results [Aggeler, P. M. et al. *Trans. 6th Congress, Internat. Soc. Hematol. Grune & Stratton*, N.Y., pgs. 490–497 (1956)]. The process was later published in detail, and it was pointed out that the process was never commercialized because the Albumin and Plasma Protein Fraction obtained as by-products were contaminated with potentially hazardous levels of barium [Hink, J. H. and Johnson, F. F., The Hemophilias, CH. 18, page 156, edited by Brinkhous, Univ. of North Carolina Press (1964)]. Biggs et al. in England [*Brit. J. Haematol.* 7:349–364 (1961)] and Janiak and Soulier [*Thromb. et Diath. Haemorr.* 8:406–424 (1962)] in France later prepared Factor IX by a similar process, substituting tricalcium phosphate for the barium sulfate. However, spontaneous formation of thrombin always occurred and it was always necessary to add heparin, both during and after processing to neutralize the potentially dangerous thrombin.

Tullis et al. [*New Eng. J. Med.* 273:667–674 (1965)] have prepared and studied a somewhat similar plasma fraction, which they refer to as "prothrombin complex". In the Tullis process, the blood was collected through a calcium-removing ion exchange resin, and the resulting resin-plasma adsorbed onto DEAE cellulose. Elution was accomplished with a sodium phosphate-sodium chloride buffer stabilized with EDTA. Clinical studies on the "prothrombin complex" are described in the reference, but other data characterizing the complex are not available.

In U.S. Pat. No. 3,717,708 (hereinafter referred to as '708) there is described a lyophilized mixture of coagulation components of human origin useful in the treatment of patients, who bleed due to a congenital or acquired deficiency of one or more of the coagulation Factors II, VII, IX, X, prepared from human plasma collected in a citrate anticoagulant, free of heparin, free of thrombin, free of the activated form of Factor X, free of depressor activity, free of anti-complement activity, and comprising the coagulation components Factors II, VII, IX, X in essentially the same proportions as normal human plasma and of a potency equivalent to a specific activity of more than 0.5 clinical unit of each component per milligram of protein.

The product of '708 is produced by a process which comprises the steps of applying Cohn Supernatant I, Method 6, from unmodified citrated human plasma onto an ion exchange resin consisting essentially of cross-linked dextran chains with diethylaminoethyl groups attached by ether linkages to the glucose units of the polysaccharide chains, and adsorbing thereon said coagulation components of the plasma; selectively eluting the column with ammonium bicarbonate solution of a pH of from about 7.3 to about 8.2 and increasing molarity; separating the eluate fraction containing coagulation components; freezing the separated eluate fraction and removing the ammonium bicarbonate therefrom by lyophilizing the frozen fraction.

A method of producing a blood-coagulation-promoting preparation from human blood plasma is described in U.S. Pat. No. 4,160,025. The product was termed FEIBA for Factor VIII Inhibitor Bypassing Activity substance. In the production of FEIBA citrated human plasma is treated with a water-insoluble inorganic coagulation-physiologically-surface-active substance in the absence of free calcium ions to generate FEIB-activity. After separation from the above substance the supernatant is treated with an anion exchanger to adsorb FEIBA and coagulation Factors II, VII, IX, and X. The adsorbed materials are eluted from the exchanger with 3% sodium chloride (0.51 mole per liter) and 0.1% trisodium citrate dihydrate (0.0033 mole per liter). The eluate is dialyzed, frozen, and lyophilized.

A concentrate containing Factors II, IX, and X was prepared by Dike et al. (*British Journal of Haematology,* 1972, Vol. 22, pages 469–490). Blood plasma was diluted to one-third its volume with distilled water and adsorbed onto DEAE-cellulose in a chromatographic column. The column was washed with 0.02 M sodium citrate and then eluted with an aqueous solution of 0.1 M sodium chloride, 0.01 M-phosphate, and 0.01 M-citrate to give a Factor VII concentrate. Next, the column was eluted with 0.25 M sodium chloride, 0.01 M-phosphate, and 0.01 M-citrate to yield a concentrate containing Factors II, IX, and X.

Middleton et al. in *Vox Sang.,* 1973, Vol. 24, pages 441–456, described a therapeutic concentrate of coagulation Factors II, IX, and X from citrated, Factor VIII-depleted plasma. After dilution of the plasma to one-third its volume with water for injection, the plasma was contacted with a DEAE-cellulose column to adsorb the coagulation Factors. Then, the cellulose was washed with an aqueous solution containing 0.03 M-phosphate and 0.03 M-citrate and eluted with an aqueous solution containing 0.03 M-phosphate, 0.03 M-citrate, and 0.2 M sodium chloride to give a concentrate of Factors II, IX, and X. This concentrate contained thrombin in amounts greater than the limits set by the U.S. National Institutes of Health. The authors note that the presence of phosphate is required in the eluting medium.

In *Vox Sang.,* 1977, Vol. 33, pages 37–50, Suomela et al. described a method for large-scale preparation of a coagulation Factor IX concentrate. Coagulation Factors II, VII, IX and X from human plasma are adsorbed onto DEAE Sephadex. The gel was washed with an aqueous buffer solution containing 0.16 M sodium chloride and 0.04 M-phosphate and then eluted with a mixture of 0.5 M and 1.0 M phosphate buffer to give a Factor IX concentrate. The Factor IX:Factor VII ratio of this product was about 2:1 to 3:1 and the Factor IX:NAPTT ratio was about 3:1. The thrombin activity of the above concentrate was lower than 0.001 Units per milliliter.

SUMMARY OF THE INVENTION

I have discovered novel methods for producing blood coaglation complexes comprising coagulation Factors II, VII, IX, and X (hereinafter referred to as "Factor IX concentrates"). Surprisingly, the novel Factor IX concentrates produced by the method of my invention possess at least about 50% more activity than the '708 products.

In the method of the invention a blood plasma fraction containing coagulation Factors II, VII, IX, and X in non-activated form is applied to an anion (basic ion) exchanger to adsorb the coagulation Factors. Next, the exchanger is washed with an aqueous solution containing a non-volatile salt and citrate ions and having an ionic strength sufficient to remove less strongly bound blood plasma proteins from the exchanger but insufficient to remove the adsorbed coagulation Factors from the exchanger. Then, the exchanger is treated with an aqueous solution containing a non-volatile salt and citrate ion and having an ionic strength sufficient to elute the adsorbed coagulation Factors but insufficient to remove those blood plasma proteins more strongly bound to the anion exchanger.

The eluate is treated to reduce its concentration of non-volatile salt and concentrated to yield the product of the invention.

The combined wash step and elution step, both with an aqueous solution containing a non-volatile salt and citrate ions, may be viewed as a selective elution of the exchanger by increasing the ionic strength of the aforementioned aqueous solution in the absence of phosphate ions.

It is important that blood coagulation complexes or concentrates do not contain thrombin since the injection of thrombin into a human would be considered highly dangerous. Although it is possible to neutralize thrombin activity with heparin, it would be preferable not to have the thrombin there in the first place. Heparin is undesirable in a Factor IX containing concentrate because it also is potentially hazardous to the patient and because it causes difficulties in assaying the coagulation factors in the concentrate. In the administration of a Factor IX containing concentrate, constant monitoring of the patient's coagulation status is required, and the presence of heparin will not only complicate this testing procedure, but will make the results thus obtained unreliable. An advantage of this invention is that the concentrate be free of both thrombin and of heparin.

Another advantage of this invention is the provision of a concentrate free of the anticomplement activity which is so often associated with plasma globulins and which would make the intravenous administration of the product highly dangerous.

An important advantage of the invention is that the product thereof has substantially reduced thrombogenicity in comparison to the prior art concentrates.

A further advantage of the product of the invention is that the ratio of Factor IX to Factor VII is substantially greater than that for the '708 product. Thus, the present Factor IX concentrate contains less Factor VII than does the '708 material. The present product, therefore, has a decreased ability to contribute to hemostasis.

DESCRIPTION OF THE PREFERRED EMBODIMENTS

The product of the invention is prepared from human blood plasma. The preponderance of blood generally taken and available for transfusion is protected from coagulation by treatment with a citrate anticoagulant which allows the blood to be utilized for only a limited period of time. After this limited time expires, this blood must be discarded or it can be made available for fractionation into certain useful components. As a matter of fact, the major source of whole blood converted to plasma for fractionation comes from blood collected by plasmapheresis, which has been protected by citrate anticoagulation. It is, therefore, important that processes for the fractionation of plasma, such as to obtain a Factor IX containing concentrate, be directed to citrate preserved blood, to which the instant method is.

As mentioned above, in the first step in the process of the invention a human blood plasma fraction containing coagulation Factors II, VII, IX, and X is contacted with a basic ion exchanger on which the coagulation Factors are adsorbed. A number of fractionation methods have been applied to human blood plasma, and these methods are summarized in "The Plasma Proteins", second edition, Vol. III, pages 548-550, Academic Press, New York, N.Y. (1977). The preferred starting material in the process of the invention is Effluent I (Cohn Supernatant I) from a Cohn fractionation method [U.S. Pat. No. 2,390,074 and *J. Am. Chem. Soc.*, Vol. 68, page 459 (1946)]. Effluent I is contacted with an anionic or basic ion exchanger, for example, DEAE (diethylaminoethyl) Sephadex ® consisting of cross-linked dextran chains with diethylaminoethyl groups attached by ether linkages to the glucose units of the polysaccharide chains, supplied by Pharmacia Fine Chemicals, Inc., Piscataway, New Market, N.J., to adsorb the aforementioned coagulation Factors. The spent Effluent I is returned to the plasma fractionation process so that none of the other plasma components is wasted.

Generally, contact between Effluent I and DEAE Sephadex ® is achieved by forming a bed of freshly equilibrated DEAE Sephadex ® and passing Effluent I therethrough. Approximately 10 g. (wet weight) of DEAE Sephadex ® per liter of Effluent I is used although the amounts employed may be varied over a wide range.

The anion exchanger is washed next to remove those plasma proteins, including ceruloplasmin, that are less strongly bound to the exchanger than the coagulation Factors. The wash solution should contain a non-volatile salt and have an ionic strength sufficient to remove these less strongly bound plasma proteins but insufficient to remove the adsorbed coagulation Factors. The ionic strength (I) of the wash solution should be about 0.10-0.45. A suitable non-volatile salt is sodium chloride in a concentration of 0.1-0.3 M. It is necessary that this aqueous sodium chloride solution contain citrate ions (sodium citrate or the like) at a concentration of about 0.05-0.2 M. A preferred wash solution in accordance with the invention is 0.2 M sodium chloride containing 0.1 M sodium citrate (I=0.26). Other aqueous salt solutions may be employed with the proviso that the salt be non-volatile and physiologically compatible with the final product. Generally, the pH of the aqueous solution should be about 6 to 9, preferably, about 7 to 8.

Prior to this wash step it may be desired to wash the anion exchanger specifically to remove ceruloplasmin. To this end the exchanger can be washed with an aqueous solution of a volatile salt such as ammonium bicarbonate, about 0.1-0.3 M. Generally, the concentration of volatile salt should be sufficient to remove the ceruloplasmin but insufficient to remove the adsorbed coagulation Factors.

The anion exchanger, having been washed as described above, is treated with an aqueous solution containing a non-volatile salt and citrate ions and having an ionic strength sufficient to elute the adsorbed coagulation Factors but insufficient to remove those plasma proteins more strongly bound to the exchanger. For this purpose the ionic strength of the aqueous solution should be greater than 0.50, preferably 0.81, and within the range of about 0.50-2.5. Thus, the solution should contain 0.35-2.0 M non-volatile salt and 0.005-0.02 M citrate ions. It is preferred that the eluting solution contain the same non-volatile salt as the aforementioned wash solution. A preferred eluting solution, then, is 0.35-2.0 M aqueous sodium chloride containing 0.005-0.02 M citrate ions. The pH of the eluting solution should be about 6 to 9, preferably about 7 to 8.

The eluate is treated to reduce its water content and the concentration of non-volatile salt, i.e., reduce the concentration of salt in the eluate, to a physiologically acceptable level, i.e., to 0.15 M or less. The aforementioned objective may be accomplished, for example, by using a combination of ultrafiltration and diafiltration as is known in the art. It is preferred that the ultrafiltration and diafiltration be carried out against an aqueous sodium chloride-sodium citrate buffer in final container concentration, i.e., the concentration of the above as found in the final container. Generally, final container concentration of sodium chloride is 0.088 M and of sodium citrate, 0.05 M. Other means of achieving removal of the salt will be suggested to those skilled in the art. It is to be noted that reduction of the amount of water may be accomplished by other methods with the exception of lyophilization, which is to be avoided.

The Factor IX concentrates can be formulated into pharmaceutical preparations for therapeutic, diagnostic, or other uses. To prepare them for intravenous administration the compositions are dissolved usually in water containing physiologically compatible substances such as sodium chloride, glycine, and the like and having a buffered pH compatible with physiological conditions. Generally, guidelines for intravenously administered compositions are established by governmental regulations.

The product prepared in accordance with the above method is characterized as substantially free of thrombogenicity and free of thrombin, heparin, thromboplastin activity, anticomplement activity, depressor activity, and activated Factor X, comprising coagulation Factors II, VII, IX and X. It has a specific activity of at least about 1.5 Factor IX units per mg. total protein. One Factor IX unit is defined as that amount of Factor IX activity contained in one ml. of fresh average pooled plasma.

The product of this invention contains no greater amounts of calcium-activated factors, such as activated Factor II (Factor IIa) and activated VII (Factor VIIa) than in concentrates of Factor II, VII, IX, and XI that have not been treated with calcium. Factors IIa and VIIa are undesirable because they potentiate intravascular coagulation of blood. It is known that calcium will activate vitamin K dependent factors such as Factor II and Factor VII. Since the present method does not involve the use of added calcium or calcium derivatives, these calcium-activated factors will not be present in an amount greater than that found in concentrates not treated with calcium. The present product also contains no greater amounts of Factor VIII Inhibitor Bypassing Activity substance than that found in concentrates of Factors II, VII, IX, and XI that have not been treated with a material which would produce a Factor VIII Inhibitor Bypassing Activity substance in such concentrates. For example, in U.S. Pat. No. 4,160,025 mentioned above, human plasma was treated with a water-insoluble inorganic coagulation-physiologically-surface-active substance in the absence of free calcium ions to generate a Factor VIII Inhibitor Bypassing Activity substance. The present method is free from the use of any such agent or material.

The product of this invention has a Factor IX:ceruloplasmin ratio of at least about 25:1, preferably 30:1 to 50:1. This ratio results from the fact that a ceruloplasmin-removing step is employed in the present method. As described above, a volatile salt such as ammonium bicarbonate, about 0.1-0.3 M is employed specifically to remove ceruloplasmin from the anion exchanger containing the adsorbed coagulation Factors.

The Factor II Specific Activity of my product is about 1.0 to 4.0, usually 1.0 to 2.0, Units per milligram of total protein. The Factor IX:Factor VII ratio of my product is at least about 6:1 or more, preferably 9:1 or more. The Factor IX:Factor II ratio and the Factor IX:Factor X ratio are about 1:1 to 2:1. Factor IX:-NAPTT is about 5:1 or greater.

A modification of the product of this invention is the product in an electrolyte buffer suitable for intravenous administration as follows:

The ultrafiltered/dialfiltered eluate is sterilized by filtration through a sterile 0.2 micron porosity membrane filter and aseptically filled in convenient portions into sterile bottles, frozen and lyophilized and stored at 5° C.

For human administration, the content of the vial is aseptically redissolved in water for injection. Alternatively, the product can be sterile filled and lyophilized to a water-free product. In this instance it is reconstituted with a suitable isotonic diluent prior to human injection.

The above process recites the details which are preferred at this time. However, many variations can be made without departing from the general principles of the invention.

For example, the amount of DEAE Sephadex relative to the volume of Effluent I may be varied over a wide range. The use of larger amounts of DEAE Sephadex will result in a lower degree of purity and greater yield of the coagulation complex, and a greater loss of other plasma proteins normally recoverable in subsequent steps. The use of smaller amounts of DEAE Sephadex will result in even higher degrees of purity, but will also result in considerably lower yields. Although DEAE Sephadex is the preferred anionic exchanger, presumably other anionic adsorbents would work also.

The elution step with an aqueous solution containing a non-volatile salt and citrate ions is extremely important to the process of this invention. Only in this fashion is there obtained a product having at least about 50% more activity than the '708 product. Furthermore, it is only in this manner that a less thrombogenic product can be secured.

Another aspect of the present invention concerns an improvement in the '708 process wherein a combined ultrafiltration-dialfiltration is used in place of lyophilization to remove ammonium bicarbonate. It has been found that the specific activity of the product prepared by the improved method of the invention is greater than that of the '708 product and, more important, the new product is substantially free of thrombogenicity. The advantages of the present invention can be obtained by applying a combination of ultrafiltration and diafiltration to the '708 eluate after its separation from the anion exchanger in order to remove ammonium bicarbonate and water therefrom. The eluate is subjected first to diafiltration to remove substantially all the ammonium bicarbonate. The eluate, therefore, is contacted with a semi-permeable membrane until the ammonium bicarbonate level is reduced to less than about 0.01 M. Membranes suitable for the diafiltration should have a nominal molecular weight cut-off of about 10,000-80,000 daltons. Typical membranes suitable for this step of the process of the invention are Amicon PM10 and Amicon H10 P10 (Amicon Corp., Lexington, Mass., Millipore PTGC (Millipore Corp., Bedford, Mass.), and Romicon PM10 and Romicon GM80 (Romicon Corp., Wicoburn, Mass.).

Following the diafiltration the eluate is subjected to ultrafiltration by contacting it with a suitable semi-permeable membrane until the desired level of water removal has been obtained. Membranes suitable for this step of the process of the invention should have a nominal molecular weight cut-off of about 10,000-80,000 daltons. Typical membranes suitable for the ultrafiltration step are those enumerated above for the diafiltration procedure.

In a preferred embodiment of the invention ultrafiltration of the eluate is conducted with hollow fibers in an ultrafiltration unit such as, for example, the Amicon DC30 (30 sq. ft. filtration area/hollow fiber unit) using an ultrafiltration membrane such as the Amicon PM10 (10,000 daltons molecular weight cut-off) or the equivalent.

After ultrafiltration the material is adjusted for pH, sterile filtered, sterile filled and lyophilized.

EXAMPLES

The invention is demonstrated further by the following illustrative examples.

ASSAY METHODS

Factors II and VII: Factor II and Factor VII were assayed by the method of Owren described in the *Scand. J. Clin. and Lab. Investigation*, Vol. 1, page 81 (1949).

Factors X and Xa: Factor X and Factor Xa were assayed by the method of Bachmen et al, described in *Thromb. Diath. Haemorrh.*, Vol. 2, page 24, (1958).

Thrombin: The assay procedure employed was described by Fenton II et al, in *Thrombosis Res.*, Vol. 4, pages 809-817 (1974).

Factors IX and VIII: Modification of the procedures described by Langdell et al (partial thromboplastin time technique), *J. Lab. Clin. Med.*, Vol. 41, pages 637-647 (1953) and Proctor et al (kaolin clotting time method) *Amer. J. Clin. Path.*, Vol. 36, page 212 (1961) were employed. Platelet Factor 3 was supplied by a cephalin suspension. Maximum surface contact activation was achieved with Celite powder. All other clotting factors (except Factor IX or Factor VIII) were supplied by a substrate comprising plasma from a patient severely deficient in Factor IX or Factor VIII mixed with barium sulfate adsorbed beef plasma. Quantitation of an unknown specimen was made by comparing its clotting time in the test with that achieved by dilutions of a normal standard.

The exact assay procedure is the same for both Factor IX and Factor VIII except that the activator in Factor IX assay is Platelin Plus Activator instead of automated APPT reagent (General Diagnostics, Inc., Morris Plains, N.J.).

Non-Activated Partial Thromboplastin Time (NAPTT): A 0.1-ml. sample of NAPTT Substrate Plasma (stored on ice), a 0.1-ml. sample of Partial Thromboplastin with no activator (stored on ice), and 0.1-ml. of the sample to be tested (in various dilutions) were added to a 10×75 mm polystyrene test tube, mixed by shaking carefully and placed in 37° C. water bath with simultaneous starting of a stopwatch. After exactly a one-minute period, 0.1 ml 0.025 M $CaCl_2$ maintained at 37° C. was added with simultaneous starting of the timer and the contents of the tube were mixed by careful shaking. Thereafter, the tube was held undisturbed for 30 seconds to 1 minute, depending upon the type of sample. It was then tilted from time to time until gelation started or a clot was observed with care being taken to minimize exposure to room temperature which was below 37° C. Time was recorded at the first sign of a clot formation. Development of opacity and gelation preceded the formation of a firm clot.

When the sample was replaced by Tris buffer, NAPTT blank time was obtained. If the blank time was over 300 seconds, the assay was continued. Any substrate plasma which gave a blank time of less than 300 seconds was unacceptable for this test.

By obtaining NAPTT times at a wide range of dilutions and plotting times in seconds on ordinate and dilutions on abscissa, a straight line relation was obtained. In most prothrombin complex concentrates, inhibitory effect was observed at low dilutions. Therefore, a straight line relationship was observed at 1:100 and higher dilutions. By using a suitable standard such as Factor IX-1 (FN-1) of the Bureau of Biologics and assigning 100 units per ml for this standard, it was possible to construct a standard curve. On this standard curve, the NAPTT times of a given sample were read and expressed as units. Longer NAPTT times (close to blank time) expressed as low NAPTT units/ml indicate reduced thrombogenicity.

EXAMPLE 1

Effluent I (1500 liters) was contacted with 15 kg. of DEAE Sephadex gel and mixed together. After two hours the mixture was filtered to give 15 kg. of gel which was washed sequentially with 50 liters of 0.2 M ammonium bicarbonate, 50 liters of 0.3 M ammonium bicarbonate and 45 liters of 0.01 M sodium citrate-0.2 M sodium chloride (pH 7.1) buffer. Elution was carried out with 33.7 liters of 0.01 M sodium citrate-0.75 M sodium chloride at pH 7.24 to obtain a protein solution of $A_{280}=10.2$. This was concentrated by ultrafiltration to $A_{280}$ of about 38.2 and diafiltered to 5 volume exchange against 0.05 M sodium citrate-0.088 M sodium chloride (pH 7.19) buffer.

The above material was sterile filtered, sterile filled in vials (20 ml. fill volume) and freeze dried. The contents of the vials were assayed by the aforementioned methods. The results are summarized in Table 1.

TABLE 1

| Coagulation Factors (U/ml) | | | | Specific Activity | NAPTT | |
|---|---|---|---|---|---|---|
| II | VII | IX | X | $(U/mg)^a$ | $(sec)^b$ | (U/ml) |
| 29 | 4.3 | 51.7 | 36 | 2.21 | 248 | 7.2 |

[a]Units IX per mg. of total protein
[b]1:100 dilution

EXAMPLE 2

Effluent I (1300 liters) was contacted with 13 kg. of DEAE Sephadex gel and mixed together. After two hours the mixture was filtered to give 13 kg. of gel which was washed sequentially with 50 liters of 0.2 M ammonium bicarbonate, 55 liters of 0.3 M ammonium bicarbonate and 45 liters of 0.01 M sodium citrate-0.2 M sodium chloride (pH 7.18) buffer. Elution was carried out with 36.5 liters of 0.01 M sodium citrate-0.75 M sodium chloride (pH 7.16) to obtain a protein solution of $A_{280}=9.65$. This was concentrated by ultrafiltration to $A_{280}=29.3$ and diafiltered to 5 volume replacement against 0.05 M sodium citrate-0.088 M sodium chloride (pH 7.16).

The above material was sterile filtered, sterile filled (20 ml fill volume) and freeze dried. The contents of the vials were assayed by the aforementioned methods. The results are outlined in Table 2.

TABLE 2

| Coagulation Factors (U/ml) | | | | Specific Activity | NAPTT | |
|---|---|---|---|---|---|---|
| II | VII | IX | X | (U/mg) | $(sec)^a$ | (U/ml) |
| 24 | 5.4 | 37 | 39 | 1.53 | 272 | 5.8 |

[a]1:100 dilution

EXAMPLE 3

Table 3 contains a side-by-side comparison of the products of Examples 1 and 2 and products prepared by the process of '708 (as described at columns 3 and 4).

TABLE 3

| Product | IX (U/ml) | Specific Activity (IX/mg protein) | NAPTT (U/ml) | IX/NAPTT |
|---|---|---|---|---|
| Invention[a] | 44.4 | 1.9 | 6.8 | 6.54 |
| '708[b] | 27.1 | 1.1 | 8.9 | 3.30 |

[a]Average of 2 runs
[b]Average of 5 runs

EXAMPLE 4

A comparison of the concentrations of the coagulation Factors in the product of the invention prepared in Examples 1 and 2 and the product of '708 is outlined in Table 4.

TABLE 4

| Product | Coagulation Factors (U/ml) | | | | IX/VII |
|---|---|---|---|---|---|
| | II | VII | IX | X | |
| Invention[a] | 26.5 | 4.9 | 44.4 | 37.5 | 9.44 |
| '708[a] | 18.3 | 9.5 | 26.1 | 29.3 | 2.80 |

[a]Average of 2 runs

EXAMPLE 5

The procedure of Example 2 was employed to prepare a product in accordance with the invention. The so-prepared product was assayed by the aforementioned methods and then held for a period of 8 months to determine its in vitro stability. The so-held product was assayed as above and the results are outlined in Table 5.

TABLE 5

| Product Held | Coagulation Factors (U/ml) | | | NAPTT 1:10[a] (sec.) | 1:100[a] (sec.) |
|---|---|---|---|---|---|
| | II | IX | X | | |
| 0 months | 24.2 | 38.7 | 37.5 | 161 | 259 |
| 8 months | 21.8 | 40.2 | 40.8 | 172 | 277 |

[a]Dilution

EXAMPLE 6

The procedure described in '708 columns 3 and 4 was followed to Step D to yield an eluate, which was divided into two equal parts. As a control one part was lyophilized and the powder was dissolved in 0.088 M sodium chloride-0.05 M sodium citrate at pH 6.9. The other part of the eluate was diafiltered to 5 volume replacements against the same buffer using 10,000 daltons cut-off hollow fiber membrane (Amicon PM10) followed by ultrafiltration for concentration. Five different starting lots (1–5) were investigated, and the results are summarized in Table 6.

TABLE 6

| | Diafiltration plus Ultrafiltration | | | Control | | |
|---|---|---|---|---|---|---|
| Lot No. | IX (U/ml) | Specific Activity (IX/$A_{280}$) | NAPTT$^a$ (secs) (1/100) | IX (U/ml) | Specific Activity (IX/$A_{280}$) | NAPTT$^a$ (secs) (1/100) |
| 1 | 27.6 | 1.08 | 360 | 24.6 | 0.94 | 201 |
| 2 | 24.9 | 1.07 | 290 | 14.4 | 0.94 | 240 |
| 3 | 24.1 | 1.11 | 370 | 21.6 | 0.92 | 208 |
| 4 | 30.8 | 1.10 | 340 | 27.6 | 0.70 | 152 |
| 5 | 34.8 | 1.01 | 200 | 26.8 | 0.65 | 142 |

EXAMPLE 7

The procedure described by Dike et al., *British Journal of Haematology*, 1972, Vol. 22, pp. 469–490, at 472 et seq. was followed using 9 l. of effluent I as obtained in the Cohn cold ethanol process [Cohn et al., *J. Am. Chem. Soc.*, Vol. 68, 459 (1946)] and 300 g. of DEAE cellulose, type DEAE-Sephacel. Effluent I corresponds to the ethanolic supernatant (8% EtOH) listed on page 474 of the reference. The ratio of 9 l. of this material to 300 g. of DEAE cellulose corresponds to the ratio of 60–65 l. 8% EtOH to 2 kg. DEAE cellulose used by Dike (p. 474). A column with an internal diameter of 5 cm was packed to a height of 15.2 cm with moist DEAE cellulose which corresponds to the ratio of 25–30 cm height of moist DEAE cellulose in a column 9.5 cm in internal diameter used by Dike (p. 473).

First and second protein fractions were obtained by elution carried out in the same manner using the same eluants as Dike. These fractions were analyzed for Factor II, VII, IX, and X and NAPTT activity as described in the above identified application. The results are summarized as follows:

| Protein Fraction | II | VII | IX (U/ml) | X | NAPTT (U/ml) | Factor IX / NAPTT |
|---|---|---|---|---|---|---|
| First | 0.1 | 3.7 | 0.07 | 0.2 | 3.2 | 0.02 |
| Second | 8.8 | 7.9 | 17.5 | not assayed | 10.2 | 1.7 |

EXAMPLE 8

Pooled blood plasma prior to application of the Cohn Fractionation method and a portion of Effluent I (Example 1) made from this pooled plasma were assayed for ceruloplasmin content. This Effluent I was contacted with DEAE Sephadex gel as in Example 1. After two hours the mixture was filtered and the gel was washed with 0.2 M and 0.3 M ammonium bicarbonate as in Example 1. The product of the invention was then eluted from the gel and treated as described in Example 1. The product was analyzed for ceruloplasmin content.

The pooled blood plasma was assigned a ceruloplasmin content of 1.0 Units per ml (U/ml) and the other ceruloplasmin assays were compared against the value for pooled blood plasma. Effluent 1 exhibited a ceruloplasmin content of 0.82 U/ml with a Factor IX activity of 2.3 U/ml; the ratio Factor IX:ceruloplasmin being 2.8:1. On the other hand, the product of the invention had a ceruloplasmin content of 0.67 U/ml and a Factor IX activity of 28 U/ml; the ratio of Factor IX:ceruloplasmin being 42:1.

Thus, without a wash with a volatile salt solution the Factor IX:ceruloplasmin ratio is about 1–3 U/ml. With a volatile salt wash the product of the invention exhibits a Factor IX:ceruloplasma ratio of at least about 25:1, preferably about 30:1 to 50:1 as contrasted with an expected less than about 20:1 ratio if a non-volatile salt wash is employed.

What is claimed is:

1. A sterile lyophilized storage stable concentrate for controlling bleeding in hemophilia, free of thrombin, heparin, thromboplastin activity, anticomplement activity, depressor activity, and activated Factor X, and containing coagulation Factors II, VII, IX, and X in non-activated form and containing no greater amounts of calcium-activated factors and Factor VIII Inhibitor Bypassing Activity substance than that found in concentrates of Factor II, VII, IX, and XI that have not been treated, respectively, with calcium or a water-insoluble inorganic coagulation-physiologically-surface-active material in the absence of calcium which would produce a Factor VIII Inhibitor Bypassing Activity substance in such concentrates and having a specific activity of at least about 1.5 Factor IX units per milligram of total protein and a Factor IX:Factor VII ratio of at least about 6:1, a Factor IX:Factor II ratio of about 1:1 to 2:1, a Factor IX:NAPTT ratio of at least about 5:1 on a Units per milliliter basis and a Factor II Specific Activity of about 1.0–4.0 Units per milligram of total protein.

2. A mixture of the concentrate of claim 1 and a sodium chloride-citrate electrolyte buffer suitable for intravenous injection.

3. The concentrate of claim 1 wherein the Factor IX:Factor VII ratio is at least about 9:1.

4. The concentrate of claim 1 wherein the Factor IX:ceruloplasmin ratio is at least about 25:1.

* * * * *